(12) United States Patent
Woo et al.

(10) Patent No.: US 10,663,312 B2
(45) Date of Patent: May 26, 2020

(54) VEHICLE AND CONTROL METHOD THEREOF

(71) Applicants: Hyundai Motor Company, Seoul (KR); Kia Motors Corporation, Seoul (KR)

(72) Inventors: Seunghyun Woo, Seoul (KR); Dong-Seon Chang, Hwaseong-si (KR); Daeyun An, Anyang-si (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 0 days.

(21) Appl. No.: 16/213,014

(22) Filed: Dec. 7, 2018

(65) Prior Publication Data

US 2020/0056902 A1 Feb. 20, 2020

(30) Foreign Application Priority Data

Aug. 17, 2018 (KR) .......................... 10-2018-0095870

(51) Int. Cl.
| | | |
|---|---|---|
| *G01C 21/34* | (2006.01) | |
| *G01C 21/36* | (2006.01) | |
| *A61B 5/00* | (2006.01) | |
| *A61B 5/16* | (2006.01) | |
| *A61B 5/18* | (2006.01) | |

(52) U.S. Cl.
CPC .......... *G01C 21/3484* (2013.01); *A61B 5/165* (2013.01); *A61B 5/18* (2013.01); *A61B 5/6893* (2013.01); *G01C 21/3492* (2013.01); *G01C 21/3626* (2013.01)

(58) Field of Classification Search
CPC ............ G01C 21/3484; G01C 21/3492; G01C 21/3626; A61B 5/18; A61B 5/165; A61B 5/6893
See application file for complete search history.

(56) References Cited

U.S. PATENT DOCUMENTS

| | | | |
|---|---|---|---|
| 6,269,308 B1* | 7/2001 | Kodaka | G01S 13/931 701/301 |
| 10,241,509 B1* | 3/2019 | Fields | B60W 30/0956 |
| 2006/0082437 A1* | 4/2006 | Yuhara | B60R 25/04 340/5.82 |

(Continued)

*Primary Examiner* — Babar Sarwar
(74) *Attorney, Agent, or Firm* — Morgan, Lewis & Bockius LLP

(57) ABSTRACT

A vehicle may include a detector configured to collect a biological signal of a driver and driving information of the vehicle; a communication device configured to communicate with an external server; a storage configured to store situation information and emotion tagged data received through the communication device and the biological signal of the driver; and a controller configured to acquire information about current emotion of the driver based on the biological signal of the driver, acquire information about inclination of the driver based on the driving information of the vehicle, extract emotion information corresponding to a current situation of the driver and the inclination of the driver from the emotion tagged data, compare the extracted emotion information with the current emotion information of the driver, and extract a primary situation factor having an influence on the emotion of the driver based on the comparison result.

18 Claims, 10 Drawing Sheets

(56) References Cited

U.S. PATENT DOCUMENTS

| | | | | |
|---|---|---|---|---|
| 2017/0123423 A1* | 5/2017 | Sako | ............... | G01C 21/3407 |
| 2017/0372431 A1* | 12/2017 | Perl | ............... | G07C 5/085 |
| 2018/0075565 A1* | 3/2018 | Myers | ............... | G06Q 30/02 |
| 2018/0174457 A1* | 6/2018 | Taylor | ............... | B60W 40/08 |
| 2018/0329415 A1* | 11/2018 | Aoi | ............... | B60W 50/14 |
| 2019/0204830 A1* | 7/2019 | Ogura | ............... | G08G 1/16 |

* cited by examiner

FIG. 5

| BIOLOGICAL SIGNAL \ EMOTION FACTOR | Disgust | Anger | Fear | Anxiety | Sadness | Stress | Frustration | Boredom | Neutral | Interest | Distress | Platonic Love | Romantic Love | Pleasure | Joy |
|---|---|---|---|---|---|---|---|---|---|---|---|---|---|---|---|
| GSR | .875 | .775 | .653 | .353 | .545 | | | | .655 | .545 | | | | | .353 |
| EEG | .555 | 0.864 | .878 | | .545 | | .464 | .477 | .577 | | | | .353 | | |
| Facial Expression | .545 | | .645 | | 0.817 | .545 | | | | | | | | | |

<CORRELATION BETWEEN BIOLOGICAL SIGNAL AND EMOTION FACTOR>

<EMOTION MODEL>

FIG. 7

| EMOTION | | REFERENCE PLACE /CONDITION | | | | PRIMARY SITUATION FACTOR | | | | | |
|---|---|---|---|---|---|---|---|---|---|---|---|
| | | PLACE | DAY | TIME | GSP | TRAFFIC CONDITION | ACCELERATION INFORMATION | TRAFFIC LIGHT | WEATHER | AVN | |
| ANGRY | | GANGNAM INTERSECTION | SATURDAY | 14:00 | xxxx | HEAVY TRAFFIC JAM | 5km/h | CLEAR | CLEAR | FUN MUSIC | ... → A DRIVE |
| EMOTION | | PLACE | DAY | TIME | GSP | TRAFFIC CONDITION | ACCELERATION INFORMATION | TRAFFIC LIGHT | WEATHER | AVN | |
| ANGRY | | GANGNAM INTERSECTION | SATURDAY | 16:00 | xxxx | HEAVY TRAFFIC JAM | 3km/h | CLEAR | CLOUDY | SOFT MUSIC | ... → B DRIVE |
| EMOTION | | PLACE | DAY | TIME | GSP | TRAFFIC CONDITION | ACCELERATION INFORMATION | TRAFFIC LIGHT | WEATHER | AVN | |
| ANGRY | | GANGNAM INTERSECTION | SATURDAY | 18:00 | xxxx | HEAVY TRAFFIC JAM | 2km/h | CLEAR | CLOUDY | ROCK | ... → C DRIVE |
| EMOTION | | PLACE | DAY | TIME | GSP | TRAFFIC CONDITION | ACCELERATION INFORMATION | TRAFFIC LIGHT | WEATHER | AVN | |
| HAPPY | | GANGNAM INTERSECTION | SATURDAY | 02:00 | xxxx | GOOD | 50km/h | CLEAR | RAINY | x | ... → D DRIVE |

A DRIVE, B DRIVE, C DRIVE: DRIVER WITH SAME INCLINATION

FIG. 8

| EMOTION | DAY | TIME | PLACE | TRAFFIC CONDITION | ACCELERATION INFORMATION |
|---|---|---|---|---|---|
| ANGRY | SATURDAY | 14:00 | GANGNAM INTERSECTION | HEAVY TRAFFIC JAM | 5km/h |

<CURRENT EMOTION OF DRIVER>

| EMOTION | DAY | TIME | PLACE | TRAFFIC CONDITION | ACCELERATION INFORMATION |
|---|---|---|---|---|---|
| HAPPY | SATURDAY | 14:00 | NEARBY EXPRESSWAY | SLOW | 25km/h |

<RECOMMENDED ROUTE>

VEHICLE AND CONTROL METHOD THEREOF

CROSS-REFERENCE TO RELATED APPLICATION

The present application claims priority to Korean Patent Application No. 10-2018-0095870 filed on Aug. 17, 2018, in the Korean Intellectual Property Office, the entire contents of which is incorporated herein for all purposes by this reference.

BACKGROUND OF THE INVENTION

Field of the Invention

The present invention relates to a vehicle and control method thereof, which increases the accuracy of detection of the driver's emotion in automatically detecting the driver's emotion by determining whether the detected driver's emotion has appeared due to a specific situation associated with the operation of the vehicle or other factors.

Discussion of Related Art

As artificial intelligence (AI) is provided in modern vehicles, technologies for operating in a response to the driver's emotion are emerging. For example, technologies for changing in-vehicle environments or providing driving routes to reflect the driver's emotion are emerging.

However, since the conventional technologies provide feedback in a response to only the driver's emotion obtained from biological signals of the driver without taking the driver's specific situation into account, they may not grasp what makes the driver have such emotion.

The information disclosed in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a vehicle and control method thereof, which increases the accuracy of detection of the driver's emotion in automatically detecting the driver's emotion by determining whether the detected driver's emotion has appeared due to a specific situation associated with the operation of the vehicle or other factors.

In accordance with an aspect of the present invention, a vehicle is provided. The vehicle may include a detector configured to collect a biological signal of a driver and driving information related to the vehicle; a communication device configured to communicate with an external server; a storage configured to store situation information and emotion tagged data received through the communication device and the biological signal of the driver; and a controller configured to acquire information related to current emotion of the driver based on the biological signal of the driver, acquire information related to inclination of the driver based on the driving information related to the vehicle, extract emotion information corresponding to a current situation of the driver and the inclination of driver from the emotion tagged data, compare the extracted emotion information with the current emotion information related to the driver, and extract a primary situation factor having an influence on the emotion of the driver based on the comparison result.

The controller may extract emotion information related to other drivers having the same inclination as the inclination of the driver in relation to the current situation as emotion information corresponding to the current situation of the driver and the inclination of the driver, and determine whether the extracted emotion information matches the information related to the current emotion of the driver.

The controller may be configured to control information related to emotion of the driver in the current situation to be sent for the storage or the external server to update the emotion tagged data, when the extracted emotion information does not match the information related to the current emotion of the driver.

The controller may extract the primary situation factor having the influence on the emotion of the driver from the emotion tagged data, when the extracted emotion information matches the information related to the current emotion of the driver.

The controller may assign a weight to each situation factor included in the current situation information, and determine that the information related to the current emotion of the driver is different from the extracted emotion information when a weight assigned to other situation factor is greater than a weight assigned to the primary situation factor.

The controller may be configured to control the information related to the current emotion of the driver determined to be different from the extracted emotion information and the current situation information to be sent for the external server to update the emotion tagged data.

The controller may generate a driving route to lead the current emotion of the driver to a target emotion based on at least one primary situation factor.

The vehicle may further include a display configured to display at least one of the current situation information, the extracted emotion information, and the driving route in a screen under the control of the controller.

The vehicle may further include an input device configured to receive the target emotion from the driver.

The current situation information may include at least one of current location, current time, traffic condition information, and speed of the vehicle.

In accordance with another aspect of the present invention, a control method of vehicle is provided. The method may include collecting a biological signal of a driver and driving information related to a vehicle; receiving situation information and emotion tagged data from an external server; acquiring information related to current emotion of the driver based on the biological signal of the driver; acquiring information related to inclination of the driver based on the driving information related to the vehicle; and extracting emotion information corresponding to a current situation of the driver and the inclination of the driver from the emotion tagged data; comparing the extracted emotion information with the current emotion information related to the driver; and extracting a primary situation factor having an influence on the emotion of the driver based on the comparison result.

The extracting of the emotion information may include extracting emotion information related to other drivers having the same inclination as the inclination of the driver in relation to the current situation as emotion information corresponding to the current situation of the driver and the inclination of the driver, and wherein the comparing the extracted emotion information with the current emotion information related to the driver may include determining whether the extracted emotion information matches the information related to the current emotion of the driver.

The method may further include sending information related to emotion of the driver in the current situation to the external server when the extracted emotion information does not match the information related to the current emotion of the driver.

The extracting a primary situation factor may include extracting the primary situation factor having the influence on the emotion of the driver from the emotion tagged data, when the extracted emotion information matches the information related to the current emotion of the driver.

The comparing the extracted emotion information with the current emotion information related to the driver may further include assigning a weight to each situation factor included in the current situation information, and determining that the information related to the current emotion of the driver is different from the extracted emotion information when a weight assigned to other situation factor is greater than a weight assigned to the primary situation factor.

The method may further include sending the information related to the current emotion of the driver determined to be different from the extracted emotion information and the current situation information to the external server.

The method may further include creating a driving route to lead the current emotion of the driver to a target emotion based on at least one primary situation factor.

The method may further include displaying at least one of the current situation information, the extracted emotion information, and the driving route.

The method may further include receiving the target emotion from the driver.

The current situation information may include at least one of current location, current time, traffic condition information, and speed of the vehicle.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 5 is a table showing information related to correlations between biological signals and emotional factors;

FIG. 7 is a table for explaining emotion tagged data;

FIG. 8 is a diagram for explaining how a driving route is generated based on primary situation factors;

Figure 1:
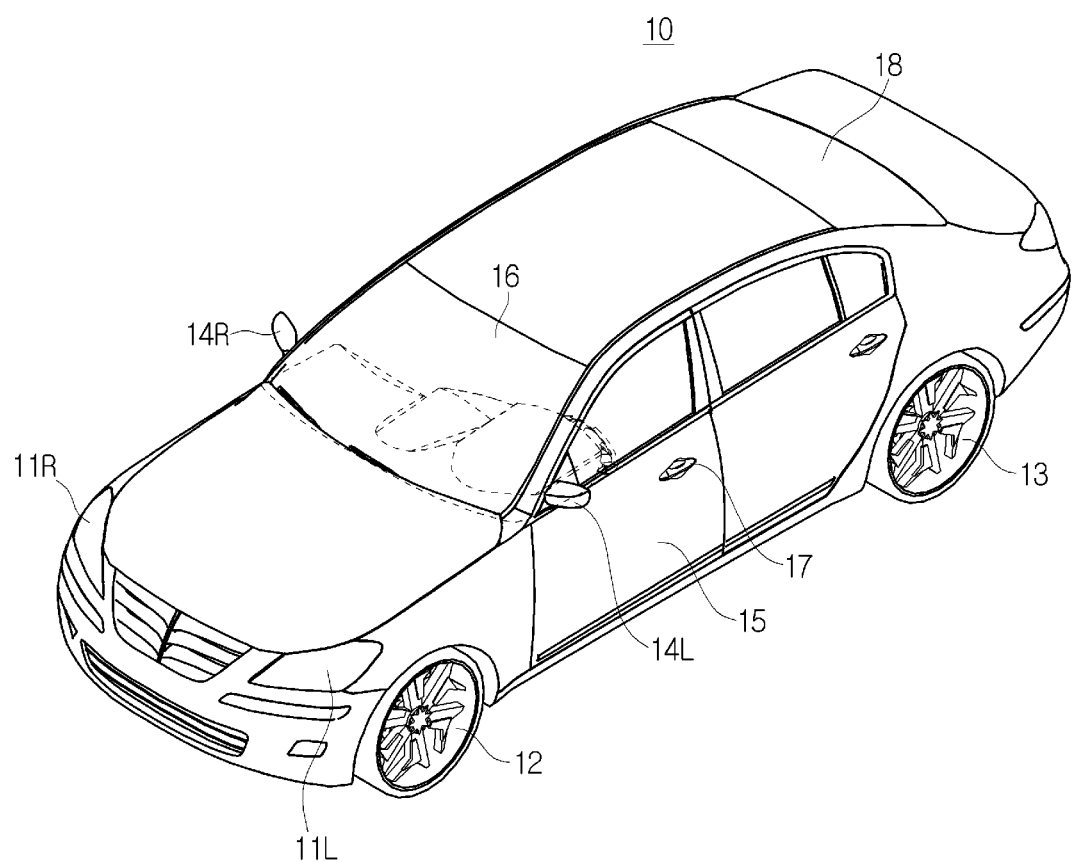
FIG. 1 shows the external of a vehicle, according to an exemplary embodiment of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION OF EXEMPLARY EMBODIMENTS

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Like numerals refer to like elements throughout the specification. Not all elements of embodiments of the present invention will be described, and description of what are commonly known in the art or what overlap each other in the exemplary embodiments will be omitted. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

It will be further understood that the term "connect" or its derivatives refer both to direct and indirect connection, and the indirect connection may include a connection over a wireless communication network.

The term "include (or including)" or "comprise (or comprising)" is inclusive or open-ended and does not exclude additional, unrecited elements or method steps, unless otherwise mentioned.

It will be understood that, although the terms first, second, third, etc., may be used herein to describe various elements, components, regions, layers and/or sections, these elements, components, regions, layers and/or sections may not be limited by these terms. These terms are only used to distinguish one element, component, region, layer or section from another region, layer or section.

The terminology used herein is for describing particular embodiments only and is not intended to limit the present disclosure. It is to be understood that the singular forms "a," "an," and "the" include plural references unless the context clearly dictates otherwise.

Reference numerals used for method steps are just used for convenience of explanation, but not to limit an order of the steps. Thus, unless the context clearly dictates otherwise, the written order may be practiced otherwise.

The principle and embodiments of the present invention will now be described with reference to accompanying drawings.

FIG. 1 shows the external of a vehicle, according to an exemplary embodiment of the present invention.

Referring to FIG. 1, a vehicle 10 in accordance with an exemplary embodiment of the present invention may include wheels 12 and 13 for moving the vehicle 10, doors 15 for shielding the internal of the vehicle 10 from the outside, a front window 16 through which the driver may see a view ahead of the vehicle 10, and side mirrors 14L, 14R for helping the driver see areas behind and to the sides of the vehicle 10.

The wheels 12 and 13 may include front wheels 12 provided in a front portion of the vehicle 10 and rear wheels 13 provided in a rear portion of the vehicle 10, and a driving system disposed within the vehicle 10 may provide turning force to the front wheels 12 or rear wheels 13 to move the vehicle 10 forward or backward thereof. The driving system may correspond to a motor that produces the turning force from electrical power supplied from a storage battery or a combustion engine that burns a fuel to generate the turning force.

The doors 15 are pivotally attached onto the left and right sides of the vehicle 10, and opened for the driver or a passenger to get in and out of the vehicle 10 and closed for shielding the internal of the vehicle 10 from the outside. Handles 17 may be mounted on the external surface of the vehicle 10 to open or close the doors 15.

The front window 16 is mounted on the upper front of the main body for allowing the driver to obtain views ahead of the vehicle 10. The side mirrors 14L and 14R include the left side mirror 14L and the right side mirror 14R placed on the left and right sides of the vehicle 10, respectively, for helping the driver obtain views behind and to the sides of the vehicle 10.

Furthermore, headlamps 11 may be disposed on the left side 11L and the right side 11R of the vehicle 10 to secure the front view of the vehicle 10.

Furthermore, the vehicle 10 may include detection devices, such as a proximity sensor for detecting an obstacle or other vehicle around the vehicle 10, a rain sensor for detecting whether it is raining and an amount of rainfall, a rotations per minute (rpm) sensor for detecting rpm, a positioning sensor for receiving global positioning system (GPS) signals to detect a current location of the vehicle 10, a speed sensor for detecting a state of motion of the vehicle 10.

The proximity sensor may send out detection signals from the side or rear of the vehicle 10 and receive a reflection signal reflected from an obstruction or other vehicle. Based on the waveform of the received reflection signal, the vehicle 10 may determine whether there is another vehicle or obstruction behind and to the sides of the vehicle 100 and where the vehicle or obstruction is.

Figure 2:
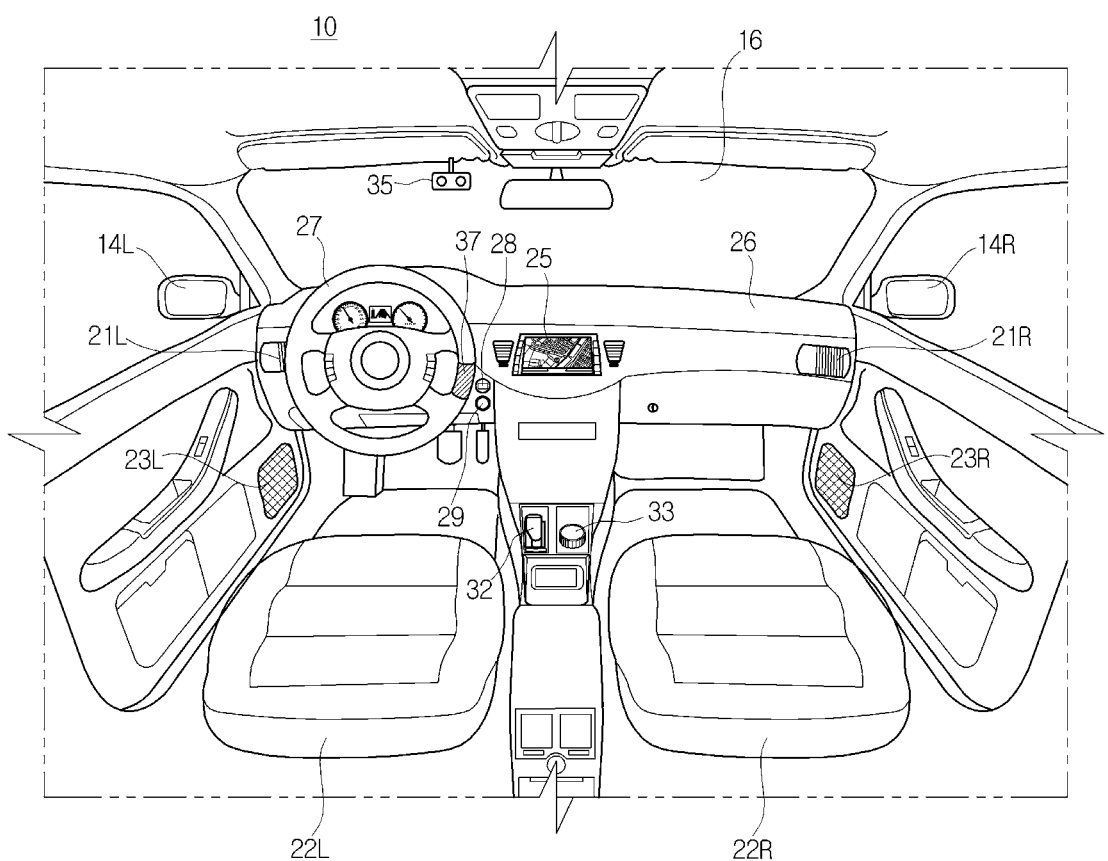
FIG. 2 shows the internal of a vehicle, according to an exemplary embodiment of the present invention.

FIG. 2 shows the internal of a vehicle, according to an exemplary embodiment of the present invention.

Referring to FIG. 2, in the center area of a dashboard 26, there may be a navigation system 25 for displaying various videos or images along with driving information related to the vehicle 10.

The navigation system 25 may provide a route to a destination or map information related to a location for the driver. Devices having such functions may be typically called a 'navigation system', but also referred to as various terms that are used by people of ordinary skill in the art.

The navigation system 25 may include a display for displaying various images and videos, which include driving information related to the vehicle 10.

Moreover, a center input device 33 of a jog shuttle type may be provided between a driver's seat 22L and a passenger's seat 22R. The driver may input a control command by turning or pressing the center input device 33 or pushing the center input device 33 to left, right, up or down.

A speaker 23 for outputting sound may be provided within the vehicle 10. The speaker 23 may output sound required in performing audio, video, navigation, and other additional functions. The speaker 23 (23L, 23R) is provided in front of each of the driver's seat 22L and the passenger's seat 22R in FIG. 2, without being limited thereto. For example, speakers may be provided in various positions within the vehicle 10.

A steering wheel 27 may be mounted on the dashboard 26 in front of the driver's seat 22L, and a key hole 28 may be formed in an area near the steering wheel 27 for a remote-control device, e.g., a key fob, to be inserted thereto. Once the remote-control device to turn on/off the ignition of the vehicle 10 is inserted or authentication between the remote-control device and the vehicle 10 is completed through a wireless communication network, the vehicle 10 may be connected to an external terminal.

Furthermore, there may be a start button 29 located on the dashboard 26 to start/stop the engine of the vehicle 10. When the remote-control device is inserted into the key hole 28 or authentication is successfully completed between the external terminal and the vehicle 10 over a wireless communication network, the engine of the vehicle 10 may be started by the user pressing the start button 29.

The vehicle 10 may also include an air conditioner to perform heating or cooling and release the heated or cooled air through vents 21 to control the temperature within the vehicle 10. The vents 21 (21L, 21R) are shown in FIG. 2 to be in front of the driver's seat 22L and the passenger's seat 22R. However, embodiments of the present invention are not limited thereto, and the vents 21 may be provided in other various positions within the vehicle 10.

Various biological signal detection devices may be provided to determine emotion of a driver who gets on the vehicle 10. The biological signal detection devices may include a camera 35 for recognizing the face or hand gestures of the driver, electrodes 37 for measuring heartbeat, a microphone for performing voice recognition, and/or the like.

Figure 3:
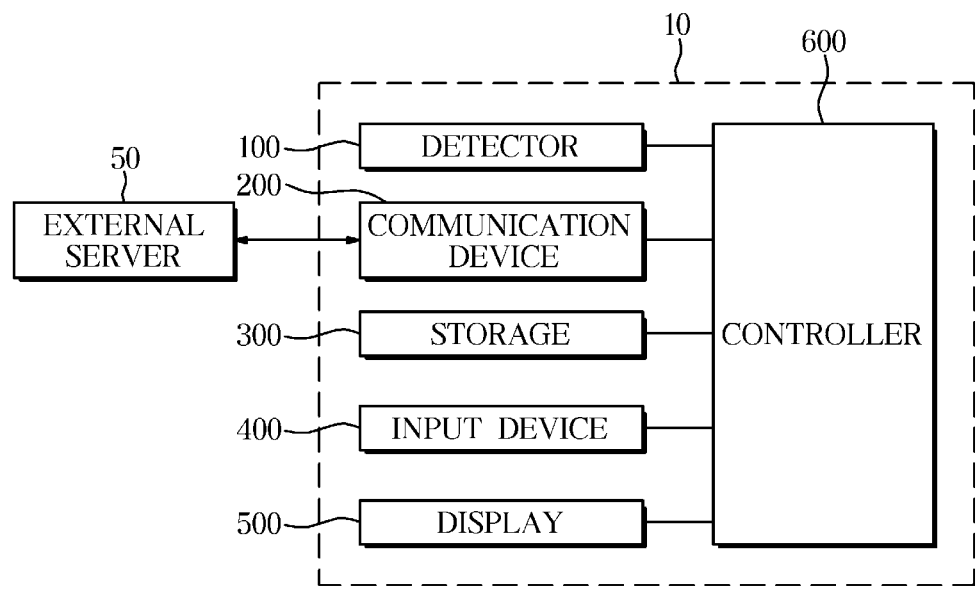
FIG. 3 is a control block diagram of a vehicle, according to an exemplary embodiment of the present invention.

FIG. 3 is a control block diagram of a vehicle, according to an exemplary embodiment of the present invention.

Referring to FIG. 3, the vehicle 10 may include a detector 100 for collecting biological signals of the driver and driving information related to the vehicle 10, a communication device 200 for communicating with an external server 50, a storage 300 for storing information collected by the detector 100 and information received through the communication device 200, an input device 400 for receiving inputs from the driver, a display 500 for displaying at least one of situation information, information related to the driver's emotion, and a driving route, and a controller 600 for controlling operation of the detector 100, communication device 200, storage 300, input device 400, and display 500.

The controller 600 may include at least one memory for storing a program for carrying out the aforementioned and following operations, and at least one processor for executing the program. The memory and the processor included in the controller 600 may be integrated in a single chip or physically separated. Embodiments of the present invention will now be described in detail.

The detector 100 may include at least one of a galvanic skin response (GSR) sensor for measuring electrical conductivity of the user's skin, a skin temperature sensor for measuring the temperature of the user's skin, a heart rate (HR) sensor for measuring the heart rate of the user, an electroencephalogram (EEG) sensor for measuring brain waves of the user, a voice recognition sensor for measuring the voice signal of the user, a surface analyzer for analyzing a facial expression of the user, and an eye tracker for tracking the pupil. The detector 100 is not limited to the aforementioned sensors, but may include any other sensors that are able to measure or collect biological signals of a human.

The detector 100 may further include a plurality of sensors for collecting driving information related to the vehicle 10. The driving information related to the vehicle 10 may include information related to steering angle and a torque of the steering wheel 27 manipulated by the driver, instantaneous acceleration, frequency and strength of the driver stepping on the accelerator, frequency and strength of the driver stepping on the brake, the number and extent of lane deviations while the vehicle 10 is driven, speed of the vehicle 10 by road type (expressway or local road), a distance to a vehicle in front, and an observance rate of car-to-car distance, etc.

Inclination of the driver observed from the driving information related to the vehicle may appear as aggressive, modest, impatient, relaxed, active, passive, etc.

The detector 100 may also collect information related to an internal situation of the vehicle 10. The internal situation information may include whether a fellow passenger is on board, information related to a conversation between the driver and a fellow passenger, multimedia play information, information related to brightness inside the vehicle, information related to a temperature inside the vehicle, etc.

The communication device 200 may communicate with the external server 50 to send or receive various information. The communication device 200 may receive outside situation information and emotion tagged data from the external device 50.

The outside situation information may include information related to a current location, current time, weather, traffic conditions, road conditions, events that has occurred on the road on which the vehicle 10 is driven. The traffic condition information may include information related to whether the current traffic condition is good or bad, and the road condition information may include information related to traffic lights, crosswalks, road type and feature, and speed limits on the road.

Hereinafter, the term 'situation information' is used as a general term that collectively refers to the driving information related to the vehicle, inside situation information, and outside situation information.

The emotion tagged data refers to data obtained by collating information related to emotions expressed by a plurality of drivers in particular situations. The emotion tagged data will be described in more detail later in connection with FIG. 7.

The communication device 200 may also receive information related to correlations between biological signals of the driver and emotion factors, and an emotion model from the external server 50. The information related to correlations between biological signals of the driver and emotion factors will be described later in connection with FIG. 5, and the emotion model will be described later in connection with FIG. 6.

The communication device 200 may send or receive data in various communication schemes. For example, the communication device 200 may use wireless fidelity (Wi-Fi), Bluetooth, Zigbee, ultra-wide band (UWB) communication, near field communication (NFC) schemes.

The storage 300 may store biological signals of the driver collected by the detector 100, outside situation information, emotion tagged data, information related to correlations between biological signals of the driver and emotion factors, information related to the driver's emotion, and emotion models. The information stored in the storage 300 may be sent to the controller 160 or to the external server 50 through the communication device 200.

The input device 400 may receive an input from the driver. The input device 400 may correspond to any device configured for receiving an input from the driver, including a touch panel of the navigation system 25 and the center input device 33 of a jog shuttle type as described above in connection with FIG. 2. The driver may input information related to his or her current emotion, information related to a target emotion, and/or a command related to an operation of the vehicle 10 through the input device 400.

The display 500 may display the current situation information, the information related to the driver's current emotion, emotion information extracted from the emotion tagged data, a driving route, and/or other various types of information. A screen displayed on the display 500 is controlled by the controller 600.

The display 500 may include a panel, and the panel may be one of a cathode ray tube (CRT) panel, a liquid crystal display (LCD) panel, a light emitting diode (LED) panel, an organic LED (OLED) panel, a plasma display panel (PDP), and a field emission display (FED) panel.

The display 500 may also include a touch panel for receiving touches of the driver as inputs. In the instant case where the display 500 includes the touch panel, the display 500 is configured as the input device 400 as well.

The controller 600 may acquire information related to the driver's current emotion based on biological signals of the driver and information related to an inclination of the driver based on the driving information related to the vehicle, extract emotion information corresponding to the current situation and inclination of the driver from the emotion tagged data to compare the emotion information with the information related to the driver's current emotion, and update the emotion tagged data according to the comparison result.

The information related to the inclination of the driver may be acquired from the driving information related to the vehicle collected by the detector 100, as described above. The inclination of the driver observed from the driving information related to the vehicle may appear as aggressive, modest, impatient, relaxed, active, passive, etc. How to acquire the information related to the driver's current emotion will be described later in connection with FIG. 5 and FIG. 6.

The controller 600 may extract emotion information related to other drivers in relation to the current situation, who have the same inclination as the inclination of the driver, from the emotion tagged data, and determine whether the extracted emotion information corresponds to information related to the driver's current emotion. Since the emotion information related to other drivers who have the same inclination as the inclination of the driver is extracted and compared with the information related to the driver's current emotion, confidence in the relation between the current situation and the driver's current emotion may increase.

When the extracted emotion information does not match the information related to the driver's current emotion, the controller 600 may control the information related to the driver's emotion in the current situation to be sent for the external server 50 to update the emotion tagged data. This is for the external server 50 to learn emotions of the driver under a particular situation.

On the other hand, when the extracted emotion information matches the information related to the driver's current emotion, the controller 600 may extract a primary situation factor that influences the emotion of the driver from the emotion tagged data.

The primary situation factor refers to common situation factors among situation factors causing the same emotion expressed by each of other drivers who have the same inclination as that of the driver at a reference place or in a reference condition.

Furthermore, the controller 600 may assign a priority to each situation factor included in the situation information and extract common situation factors in a predetermined range of priorities as the primary situation factors. The primary situation factors will be described in more detail later in connection with FIG. 7.

The controller 600 may further assign a weight to each situation factor included in the current situation information, and determine that the information related to the driver's current emotion is different from the emotion information extracted from the emotion tagged data when a weight assigned to other situation factor is greater than the weight assigned to the primary situation factor.

For example, even when information related to the driver's current emotion and the emotion information extracted from the emotion tagged data corresponding to the current situation of the driver all correspond to anger, the anger expressed by the driver may be caused from a conversation with the fellow passenger. When a weight assigned to a situation factor of the conversation with the fellow passenger is greater than a weight assigned to the primary situation factor, the anger of the driver may be determined to be caused not by the primary situation factor but by the conversation with the fellow passenger. Accordingly, in the instant case, the information related to the driver's current emotion may not be considered to match the emotion information extracted from the emotion tagged data.

Weights assigned to the situation factors may be set in advance by the driver or set in advance based on the inclination of the driver.

The controller 600 may generate a driving route to lead the driver's current emotion to the target emotion based on at least one of the primary situation factors. How to generate the driving route will be described in more detail later in connection with FIG. 8.

Accordingly, the reliance of the information related to the driver's current emotion on information related to a particular situation may be more accurately understood by assigning a weight to each of the situation factors included in the current situation information and comparing the information related to the driver's emotion with the emotion information extracted from the emotion tagged data based on the primary situation factors. In other words, whether the current emotional change of the driver is attributed to a situation associated with the operation of the vehicle or to other situation may be determined.

The vehicle 10 may generate a more optimal driving route by not reflecting the driver's emotional change caused by situations unassociated with driving in creating a driving route to make the driver's emotion better.

Figure 4:
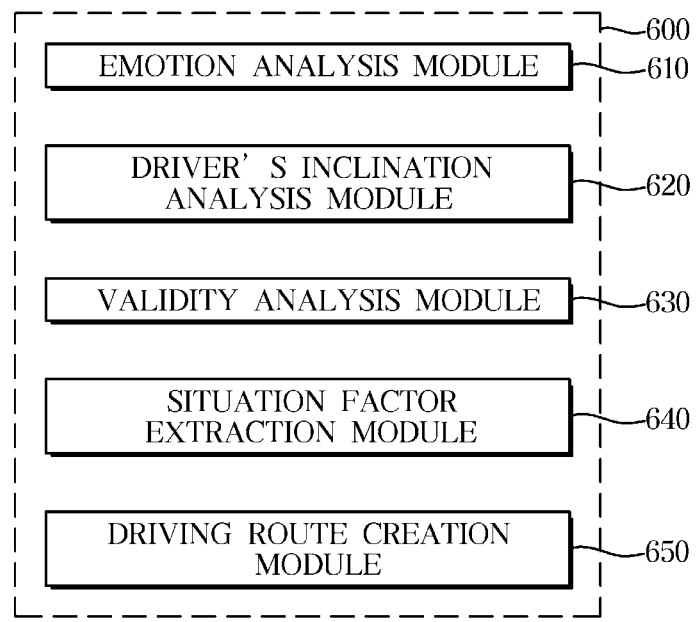
FIG. 4 is a diagram for explaining a controller of a vehicle in detail, according to an exemplary embodiment of the present invention.

FIG. 4 is a diagram for explaining a controller of a vehicle in detail, according to an exemplary embodiment of the present invention.

Referring to FIG. 4, the controller 600 may include an emotion analysis module 610, a driver's inclination analysis module 620, a validity analysis module 630, a situation factor extraction module 640, and a driving route creation module 650.

Figure 6:
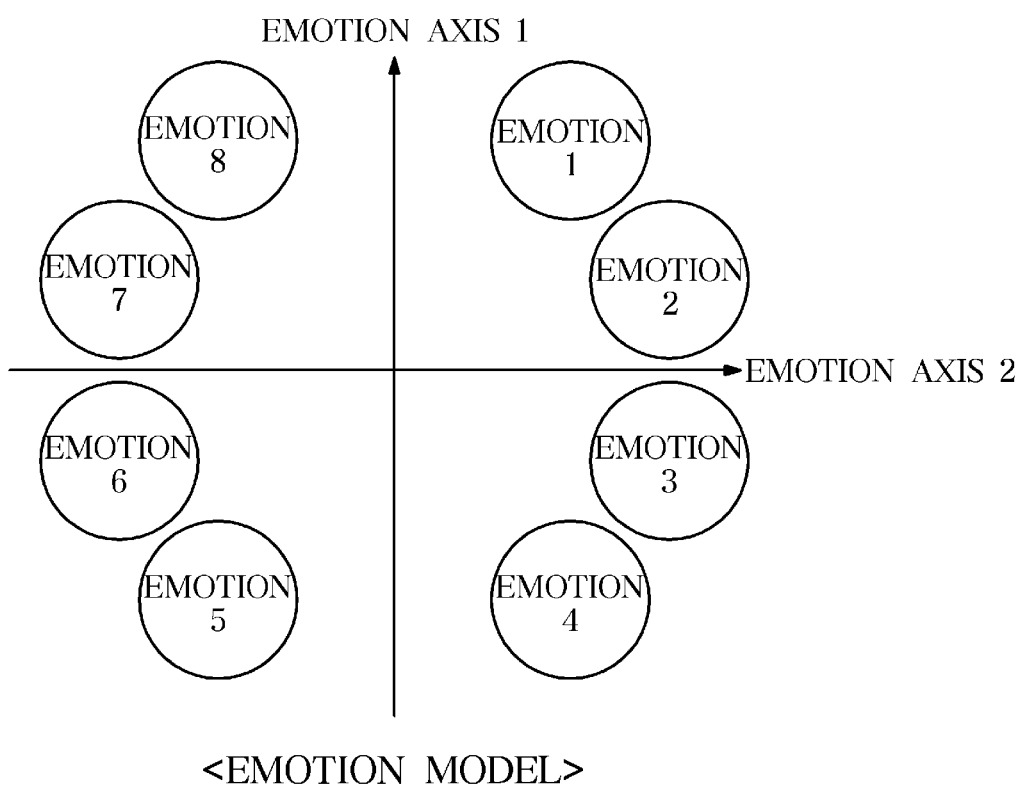
FIG. 6 shows an emotion model.

The emotion analysis module 610 may acquire information related to current emotion of the driver based on a biological signal of the driver collected by the detector 100. The emotion analysis module 610 may also acquire information related to correlations between biological signals and situation factors as shown in FIG. 5, and information related to emotion of the driver using an emotion model as shown in FIG. 6.

The driver's inclination analysis module 620 may acquire information related to inclination of the driver by analyzing driving information related to the vehicle collected by the detector 100. The driving information related to the vehicle 10 may include information related to steering angle and a torque of the steering wheel 27 manipulated by the driver, instantaneous acceleration, frequency and strength of the driver stepping on the accelerator, frequency and strength of the driver stepping on the brake, the number and extent of lane deviations while the vehicle 10 is driven, speed of the vehicle 10 by road type (expressway or local road), a distance to a vehicle in front, and an observance rate of car-to-car distance, etc. Inclination of the driver observed from the driving information related to the vehicle may appear as aggressive, modest, impatient, relaxed, active, passive, etc.

The validity analysis module 630 may extract emotion information corresponding to a current situation of the driver and the driver's inclination from the emotion tagged data and compare the emotion information with the information related to the current emotion of the driver. The validity analysis module 630 may extract emotion information related to other drivers having the same inclination as the inclination of the driver in relation to the current situation from the emotion tagged data and determine whether the extracted emotion information matches the information related to the current emotion of the driver.

The situation factor extraction module 640 may, when the emotion information extracted from the emotion tagged data matches information related to the current emotion of the driver, extract a primary situation factor that influences the emotion of the driver from the emotion tagged data. Furthermore, the situation factor extraction module 640 may assign a weight to each of the situation factors included in the current situation information.

The validity analysis module 630 may determine that the information related to the driver's current emotion is different from the emotion information extracted from the emotion tagged data when a weight assigned to other situation factor is greater than a weight assigned to the primary situation factor. Accordingly, the reliance of the information related to the driver's current emotion on information related to a particular situation may be more accurately understood by assigning a weight to each of the situation factors included in the current situation information and comparing the information related to the driver's emotion with the emotion information extracted from the emotion tagged data based on the primary situation factors.

The driving route creation module 650 may generate a driving route to lead the driver's current emotion to the target emotion based on at least one of the primary situation factors.

FIG. 5 is a table showing information related to correlations between biological signals and emotional factors.

Referring to FIG. 5, the controller 600 may obtain information related to the driver's emotion using biological signals of the driver collected by the detector 100 and information related to correlations between the biological signals of the driver and emotion factors stored in the storage 300.

In FIG. 5, values of correlations of a GSR signal with disgust and anger emotion factors are 0.875 and 0.775, respectively, which may be interpreted that the GSR signal has high relevance to disgust and anger emotion factors. Accordingly, the biological signal of the driver collected by a GSR measurer may become a basis to determine that the driver's emotion corresponds to a feeling of anger or a feeling of disgust.

In a case of a joy emotion factor, the value of a correlation with the GSR signal is relatively low, which may be interpreted that the joy emotion factor has low relevance to the GSR signal.

Furthermore, values of correlations of an EEG signal with anger and fear emotion factors are 0.864 and 0.878, respectively, which may be interpreted that the EEG signal has higher relevance to the anger and fear emotion factors than to other emotion factors. Accordingly, a biological signal of the driver collected by an EEG measurer may become a basis to determine that the driver's emotion corresponds to anger or fear.

In the present way, the controller 600 may obtain information related to the driver's emotion using the information related to correlations between biological signals of the driver and emotion factors. Pieces of the information shown in FIG. 5 are only experimental results, which may vary by experimental condition.

FIG. 6 shows an emotion model.

Referring to FIG. 6, an emotion model is shown on a graph as classification of emotions of the driver appearing in a response to biological signals of the driver. The emotion model classifies emotions of the driver with respect to predetermined emotion axes. The emotion axes may be determined based on emotions measured by sensors. For example, emotion axis 1 may correspond to positivity which may be measured by analyzing voice or facial expression of the driver, and emotion axis 2 may correspond to excitability or activity which may be measured by GSR or EEG.

When an emotion of the driver has high positivity and high excitability, the emotion may be classified into emotions 1 and 2. On the other hand, when an emotion of the driver has negative positivity, i.e., negativity, and high excitability, the emotion may be classified into emotions 3 and 4.

This emotion model may be a Russell emotion model. The Russel emotion model may be represented in a two dimensional xy-plane graph, classifying emotions into eight categories of joy at 0 degree, excitement at 45 degrees, arousal at 90 degrees, misery at 135 degrees, displeasure at 180 degrees, depression at 225 degrees, sleepiness at 270 degrees, and relaxation at 315 degrees. The eight categories have a total of 28 emotions, similar ones of which belong to each of eight categories.

The emotion model may be received from the external server 50 through the communication device 200. The controller 600 may map the information related to the driver's emotion acquired using the information related to correlations between biological signals of the driver and emotion factors to the emotion model, and control the display 500 to display the information related to the driver's emotion mapped to the emotion model.

The emotion model may also be used in setting a target emotion. For example, the information related to the driver's current emotion acquired from a result of analysis of biological signals of the driver may be mapped to emotion 5 on the emotion model. The driver's emotion corresponding to the emotion 5 may be an emotion having negativity and low excitability. Accordingly, the controller 600 may set the target emotion to an emotion corresponding to emotion 2 on the emotion model to change the driver's emotion to an emotion having positivity and high excitability. In a case that the driver's current emotion has high positivity, the controller 600 may control the current emotion to remain the same. In other words, the target emotion may be variously set based on the situation and/or current emotion of the driver.

The target emotion may also be set by an input from the driver. The driver may input a target emotion he/she wants through the input device 400.

FIG. 7 is a table for explaining emotion tagged data.

Referring to FIG. 7, the emotion tagged data is data obtained by collating information related to emotions expressed by a plurality of drivers in particular situations. The external server 50 collects and saves information related to emotions expressed by a plurality of drivers at particular time and places.

For example, the external server 50 may collect and save driver A's anger expressed in a severe traffic jam at Gangnam intersection at 2 p.m., driver B's anger expressed in a severe traffic jam at the Gangnam intersection at 4 p.m., driver C's anger expressed in a severe traffic jam at the Gangnam intersection at 6 p.m., and driver D's happiness expressed in a smooth traffic condition at the Gangnam intersection at 2 a.m.

In this regard, the situation information may include the place, time, traffic condition, acceleration information, the number of traffic lights, weather, an AVN operation state, etc., as situation factors.

Although FIG. 7 shows information related to emotions expressed by a plurality of drivers at the same place, the Gangnam intersection, at different hours, collection of emotions is not limited thereto and information related to various emotions expressed by a plurality of drivers in various situations may be collected.

In FIG. 7, the drivers A, B, and C have the same inclination as that of the driver of the vehicle 10. The controller 600 may extract information related to emotions expressed in a particular situation by other drivers having the same inclination as that of the driver from the emotion tagged data received from the external server 50. The particular situation refers to the current situation of the driver.

Primary situation factors may be extracted in the following method.

Common situation factors may be extracted as the primary situation factors from situation factors that cause the same emotion expressed by each of the other drivers who have the same inclination as that of the driver at a reference place or in a reference condition.

For example, unlike what is shown in FIG. 7, driver A may express anger in a situation of heavy traffic, bumper-to-bumper driving, many traffic lights, and loud background noise at the Gangnam intersection at around 2 p.m. In the instant case, the anger may be attributed to the heavy traffic, bumper-to-bumper driving, many traffic lights, and loud background noise, which may be situation factors for the emotion of driver A.

Driver B may express anger in a situation of heavy traffic, bumper-to-bumper driving, many traffic lights, high humidity, and high temperature at the Gangnam intersection at around 2 p.m. In the instant case, the anger may be attributed to the heavy traffic, bumper-to-bumper driving, many traffic lights, high humidity, and high temperature, which may be situation factors for the emotion of driver B.

Driver C may express anger in a situation of heavy traffic, bumper-to-bumper driving, many traffic lights, and road repair work at the Gangnam intersection at around 2 p.m. In the instant case, the anger may be attributed to the heavy traffic, bumper-to-bumper driving, many traffic lights, and road repair work, which may be situation factors for the emotion of driver C.

In the present example, all the drivers A, B, and C who have the same inclination as that of the driver express anger at the reference place, the Gangnam intersection, and among the situation factors that cause the anger, the common situation factors, which are heavy traffic, the bumper-to-bumper driving, and the many traffic lights, may be extracted as the primary situation factors.

Furthermore, a priority may be assigned to each situation factor included in the situation information and common situation factors in a predetermined range of priorities may be extracted as the primary situation factors. For example, a traffic condition, a road type, a current location, and weather may be assigned higher priorities in the listed order. In a case that the primary situation factors are set to be extracted from the situation factors in the top three priorities and the plurality of drivers commonly assign higher priorities for the traffic condition, the road type, and the current location in the listed order, the traffic condition, the road type, and the current location may be extracted as the primary situation factors.

It is assumed herein that the priorities assigned by the plurality of drivers who have the same inclination for the situation factors are the same or similar.

FIG. 8 is a diagram for explaining how a driving route is generated based on primary situation factors.

Referring to FIG. 8, the driver is now feeling angry at the Gangnam intersection, and the anger may be attributed to a heavy traffic jam. In the instant case, the primary situation factors may be extracted to be the current location and traffic condition. The controller 600 may generate a driving route based on the primary situation factors that cause the negative emotion felt by the driver to change the negative feeling to a positive feeling. For example, the controller 600 may generate a driving route by changing stops en route to a destination. As shown in FIG. 8, the controller 600 generates a driving route so that the driver may feel pleasant by driving on a nearby expressway having a moderate traffic condition.

Accordingly, the vehicle 10 provides not only the simple shortest route or a route requiring shortest time to a destination but also a driving route to make the driver's emotion better, giving the driver the experience of a more pleasant drive.

Figure 9:
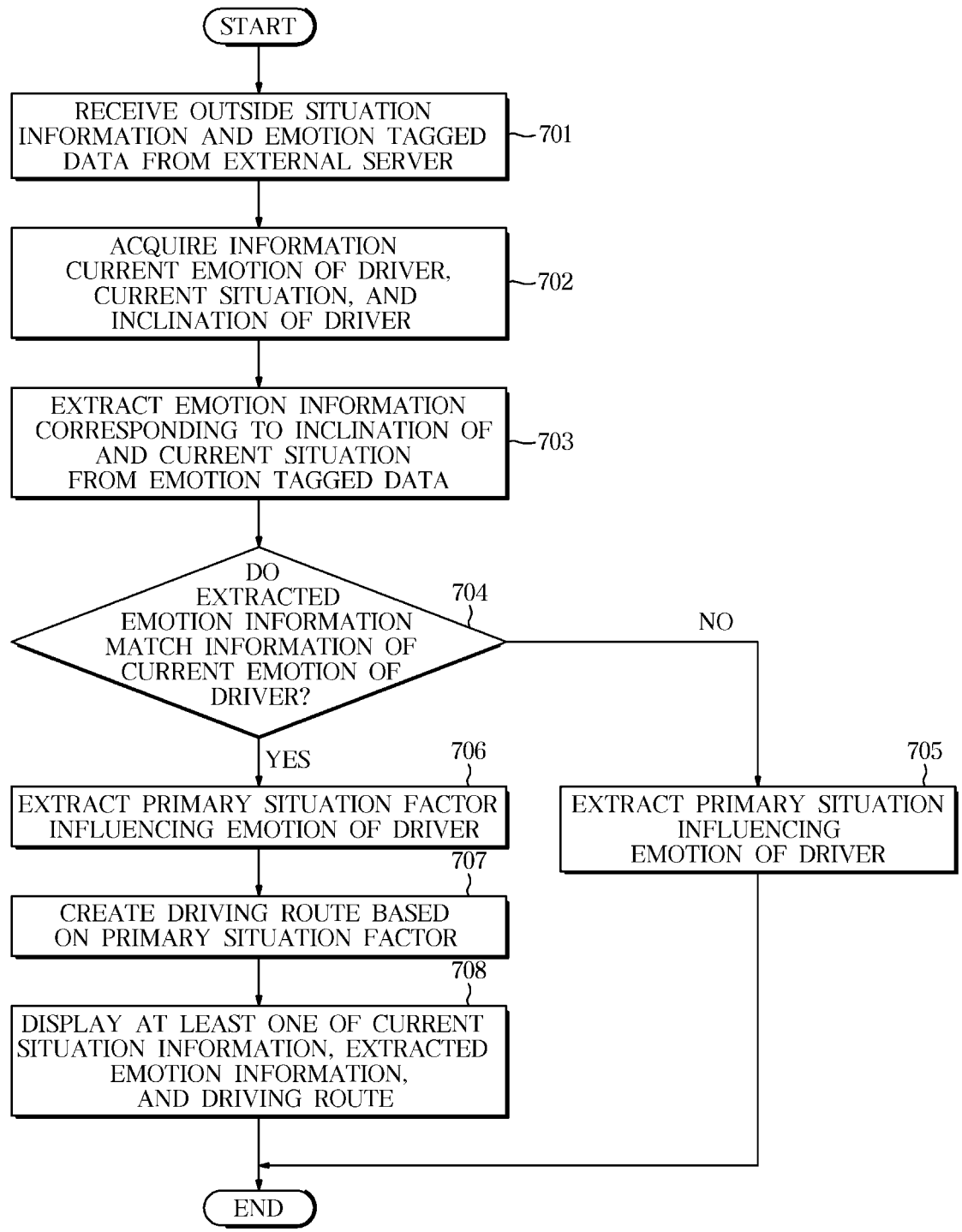
FIG. 9 is a flowchart illustrating a control method of a vehicle, according to an exemplary embodiment of the present invention.

FIG. 9 is a flowchart illustrating a control method of a vehicle, according to an exemplary embodiment of the present invention.

Referring to FIG. 9, the communication device 200 of the vehicle 10 receives outside situation information and emotion tagged data from the external device 50, in 701. The detector 100 of the vehicle 10 may collect biological signals of the driver, driving information related to the vehicle, and inside situation information. The controller 600 acquires information related to a current emotion of the driver from biological signals of the driver, information related to inclination of the driver from the driving information related to the vehicle, and current situation information by collating outside situation information, inside situation information, and the information related to driving of the vehicle, in 702.

Subsequently, the controller 600 extracts emotion information corresponding to the inclination of the driver and the current situation from the emotion tagged data, in 703. The controller 600 determines whether the emotion information extracted from the emotion tagged data matches the information related to the current emotion of the driver, in 704. When the emotion information extracted from the emotion tagged data does not match the information related to the current emotion of the driver, the controller 600 controls the information related to the driver's emotion in the current situation of the driver to be sent to the storage 300 and the external server 50 to update the emotion tagged data, in 705.

Otherwise, when the emotion information extracted from the emotion tagged data matches the information related to the current emotion of the driver, the controller 600 extracts a primary situation factor that influences the emotion of the driver from the emotion tagged data, in 706. Subsequently, the controller 600 generates a driving route to lead the current emotion of the driver to a target emotion based on at least one primary situation factor in 707, and controls the display 500 to display at least one of the current situation information, the extracted emotion information, and the driving route in 708.

Figure 10:
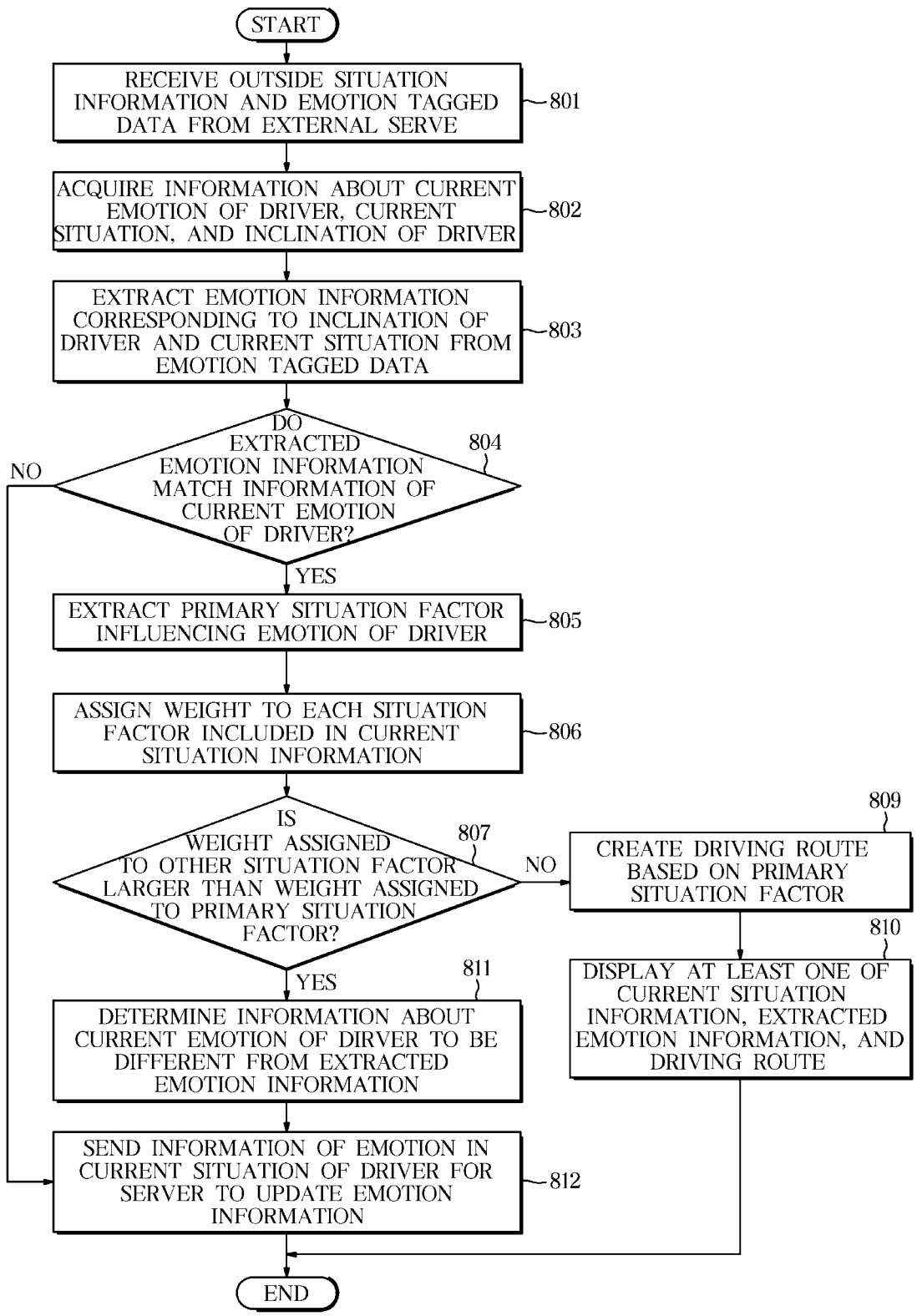
FIG. 10 is a flowchart illustrating a control method of a vehicle, according to various exemplary embodiments of the present invention.

FIG. 10 is a flowchart illustrating a control method of a vehicle, according to various exemplary embodiments of the present invention.

Referring to FIG. 10, the communication device 200 of the vehicle 10 receives outside situation information and emotion tagged data from the external device 50, in 801. The detector 100 of the vehicle 10 may collect biological signals of the driver, driving information related to the vehicle, and inside situation information. The controller 600 acquires information related to a current emotion of the driver from biological signals of the driver, information related to inclination of the driver from the driving information related to the vehicle, and current situation information by collating outside situation information, inside situation information, and the information related to driving of the vehicle, in 802.

Subsequently, the controller 600 extracts emotion information corresponding to the inclination of the driver and the current situation from the emotion tagged data, in 803. The controller 600 determines whether the emotion information extracted from the emotion tagged data matches the information related to the current emotion of the driver, in 804. When the emotion information extracted from the emotion tagged data does not match the information related to the current emotion of the driver, the controller 600 controls the information related to the driver's emotion in the current situation of the driver to be sent to the storage 300 and the external server 50 to update the emotion tagged data, in 812.

Otherwise, when the emotion information extracted from the emotion tagged data matches the information related to the current emotion of the driver, the controller 600 extracts a primary situation factor that influences the emotion of the driver from the emotion tagged data, in 805. The controller 600 assigns a weight to each of the situation factors included in the current situation information in 806, and compares weights assigned to the primary situation factor and the other situation factors in 807.

When the weight of the primary situation factor is greater than weights of other situation factors, the controller 600 generates a driving route to lead the current emotion of the driver to a target emotion based on at least one primary situation factor in 808, and controls the display 500 to display at least one of the current situation information, the extracted emotion information, and the driving route in 809.

Otherwise, when the weight assigned to other situation factor is greater than to the primary situation factor, the controller 600 determines that the information related to the current emotion of the driver is different from the emotion information extracted from the emotion tagged data in 810, and sends the information related to the driver's emotion in the current situation to the external server 50 to update the emotion tagged data in 812.

Figure 11:
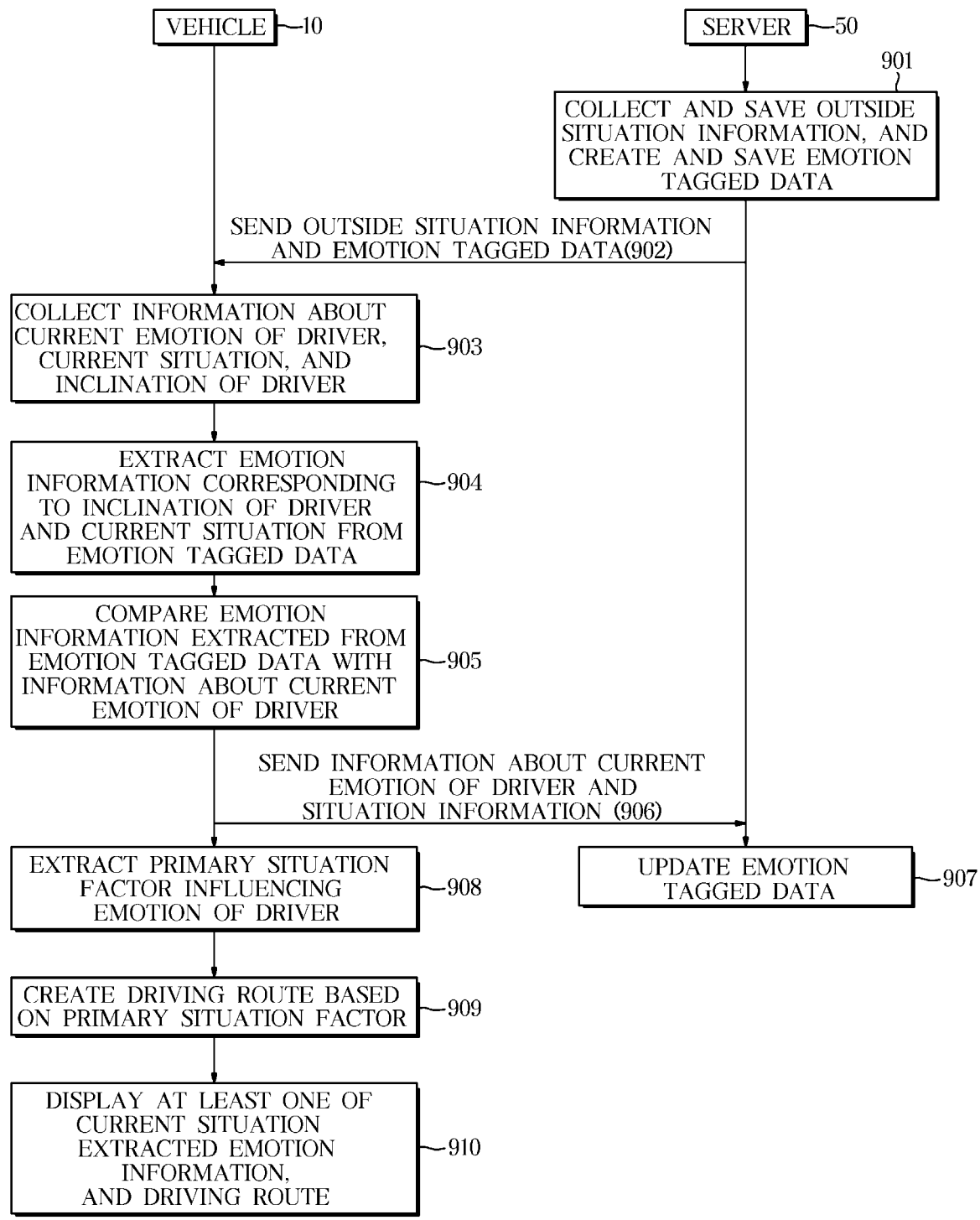
FIG. 11 is a diagram for explaining relations between a vehicle and an external server, according to an exemplary embodiment of the present invention.

FIG. 11 is a diagram for explaining relations between a vehicle and an external server, according to an exemplary embodiment of the present invention.

Referring to FIG. 11, the external server 50 collects and stores outside situation information and emotion tagged data in 901 and sends them to the vehicle 10 in 902.

The vehicle 10 may collect biological signals of the driver, driving information related to the vehicle, and inside situation information. The vehicle 10 acquires information related to a current emotion of the driver from biological signals of the driver, information related to inclination of the driver from the driving information related to the vehicle, and current situation information by collating outside situation information, inside situation information, and the information related to driving of the vehicle, in 903.

Subsequently, the vehicle 10 extracts emotion information corresponding to the inclination of the driver and the current situation from the emotion tagged data, in 904. The vehicle 10 determines whether the emotion information extracted from the emotion tagged data matches the information related to the current emotion of the driver, in 905. When the emotion information extracted from the emotion tagged data does not match the information related to the current emotion of the driver, the vehicle 10 sends the information related to the driver's emotion in the current situation to the external server 50, in 906. The external server 50 receives the information related to the driver's emotion in the current situation to update the emotion tagged data, in 907.

Otherwise, when the emotion information extracted from the emotion tagged data matches the information related to the current emotion of the driver, the vehicle 10 extracts a primary situation factor that influences the emotion of the driver from the emotion tagged data, in 908. Subsequently, the vehicle 10 generates a driving route to lead the current emotion of the driver to a target emotion based on at least one primary situation factor in 909, and displays at least one of the current situation information, the extracted emotion information, and the driving route on the display 500 in 910.

According to exemplary embodiments of the present invention, a vehicle and control method thereof may increase the accuracy of detection of the driver's emotion in automatically detecting the driver's emotion by determining whether the detected driver's emotion has appeared due to a specific situation associated with the operation of the vehicle or other factors.

Furthermore, a more optimal route for driving may be generated by not reflecting the driver's emotional change due to situations unassociated with driving in creating a driving route to make the driver's emotion better.

Meanwhile, the exemplary embodiments of the present invention may be implemented in a form of recording media for storing instructions to be conducted by a computer. The instructions may be stored in a form of program codes, and when executed by a processor, may generate program modules to perform operation in the exemplary embodiments of the present invention. The recording media may correspond to computer-readable recording media.

The computer-readable recording medium includes any type of recording medium having data stored thereon which may be thereafter read by a computer. For example, it may be a ROM, a RAM, a magnetic tape, a magnetic disk, a flash memory, an optical data storage device, etc.

For convenience in explanation and accurate definition in the appended claims, the terms "upper", "lower", "inner", "outer", "up", "down", "upper", "lower", "upwards", "downwards", "front", "rear", "back", "inside", "outside", "inwardly", "outwardly", "internal", "external", "inner", "outer", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A vehicle comprising:
    a sensor configured to collect a biological signal of a driver and driving information related to the vehicle;
    a communication device configured to communicate with an external server;
    a storage device configured to store situation information and emotion tagged data received through the communication device and the biological signal of the driver, wherein the emotion tagged data includes information related to emotions expressed by a plurality of drivers in predetermined situations; and
    a controller configured to acquire current emotion information of the driver based on the biological signal of the driver, acquire information related to inclination of the driver based on the driving information related to the vehicle, extract emotion information of the plurality of drivers having same inclination as the inclination of the driver in a current situation from the emotion tagged data, compare the extracted emotion information of the plurality of drivers with the current emotion information of the driver, and extract a primary situation factor having an influence on emotion of the driver based on the comparison result,
    wherein the controller further is configured to determine whether the extracted emotion information of the plurality of drivers matches the current emotion information of the driver.

2. The vehicle of claim 1,
    wherein the controller is configured to update the emotion tagged data by sending information related to the emotion of the driver in the current situation to the storage device or the external server, when the extracted emotion information of the plurality of drivers does not match the current emotion information of the driver.

3. The vehicle of claim 1, wherein the controller is configured to extract the primary situation factor having the influence on the emotion of the driver from the emotion tagged data, when the extracted emotion information of the plurality of drivers matches the current emotion information of the driver.

4. The vehicle of claim 3, wherein the controller is configured to assign a weight to each situation factor included in the current situation information, and determine that the current emotion information of the driver is different from the extracted emotion information of the plurality of drivers when a weight assigned to other situation factor is greater than a weight assigned to the primary situation factor.

5. The vehicle of claim 4, wherein the controller is configured to update the emotion tagged data by sending the current emotion information of the driver determined to be different from the extracted emotion information of the plurality of drivers and the current situation information to the external server.

6. The vehicle of claim 3, wherein the controller is configured to generate a driving route to lead a current emotion of the driver to a target emotion based on at least one primary situation factor.

7. The vehicle of claim 6, further including: a display configured to display at least one of the current situation information, the extracted emotion information of the plurality of drivers, and the driving route in a screen under a control of the controller.

8. The vehicle of claim 6, further including: an input device configured to receive the target emotion from the driver.

9. The vehicle of claim 1, wherein the current situation information includes at least one of current location, current time, traffic condition information, and speed of the vehicle.

10. A control method of a vehicle, the control method comprising:
collecting, by a controller, a biological signal of a driver and driving information related to the vehicle;
receiving, by the controller, situation information and emotion tagged data from an external server, wherein the emotion tagged data includes information related to emotions expressed by a plurality of drivers in predetermined situations;
acquiring, by the controller, current emotion information of the driver based on the biological signal of the driver;
acquiring, by the controller, information related to inclination of the driver based on the driving information related to the vehicle;
extracting, by the controller, emotion information of the plurality of drivers having same inclination as the inclination of the driver in a current situation from the emotion tagged data;
comparing, by the controller, the extracted emotion information of the plurality of drivers with the current emotion information of the driver; and
extracting, by the controller, a primary situation factor having an influence on emotion of the driver based on the comparison result,
wherein the comparing includes determining whether the extracted emotion information of the plurality of drivers matches the current emotion information of the driver.

11. The control method of the vehicle of claim 10, further including:
sending information related to the emotion of the driver in the current situation to the external server when the extracted emotion information of the plurality of drivers does not match the current emotion information of the driver.

12. The control method of the vehicle of claim 10, wherein the extracting a primary situation factor includes:
extracting the primary situation factor having the influence on the emotion of the driver from the emotion tagged data, when the extracted emotion information of the plurality of drivers matches the current emotion information of the driver.

13. The control method of the vehicle of claim 12, wherein the comparing further includes:
assigning a weight to each situation factor included in the current situation information, and
determining that the current emotion information of the driver is different from the extracted emotion information of the plurality of drivers when a weight assigned to other situation factor is greater than a weight assigned to the primary situation factor.

14. The control method of the vehicle of claim 13, further including:
sending the current emotion information of the driver determined to be different from the extracted emotion information of the plurality of drivers and the current situation information to the external server.

15. The control method of the vehicle of claim 12, further including:
creating a driving route to lead a current emotion of the driver to a target emotion based on at least one primary situation factor.

16. The control method of the vehicle of claim 15, further including:
displaying at least one of the current situation information, the extracted emotion information of the plurality of drivers, and the driving route.

17. The control method of the vehicle of claim 15, further including:
receiving the target emotion from the driver.

18. The control method of the vehicle of claim 10, wherein the current situation information includes at least one of current location, current time, traffic condition information, and speed of the vehicle.

* * * * *